United States Patent [19]

Beavon et al.

[11] 4,233,141
[45] Nov. 11, 1980

[54] PROCESS FOR REMOVAL OF CARBONYL SULFIDE IN LIQUIFIED HYDROCARBON GASES WITH ABSORPTION OF ACID GASES

[75] Inventors: David K. Beavon, Pasadena; Mark Mackles, Tarzana, both of Calif.

[73] Assignee: The Ralph M. Parsons Company, Pasadena, Calif.

[21] Appl. No.: 33,875

[22] Filed: Apr. 27, 1979

[51] Int. Cl.³ .................. C07C 7/11; C01B 31/26; C01B 17/16; C07C 9/10
[52] U.S. Cl. .................. 208/236; 55/37; 55/73; 423/226; 423/228; 423/243
[58] Field of Search ............ 208/236; 55/37, 56, 55/73; 423/228

[56] References Cited

U.S. PATENT DOCUMENTS

| | | |
|---|---|---|
| 2,383,416 | 8/1945 | Reed .................. 208/236 |
| 2,594,311 | 4/1952 | Johnson et al. . |
| 2,726,992 | 12/1955 | Easthagen et al. .......... 208/236 |
| 3,098,705 | 7/1963 | Bally .................. 208/236 |
| 3,100,680 | 8/1963 | Shaw et al. .............. 208/236 |
| 3,961,015 | 6/1976 | Dailey . |
| 3,966,875 | 6/1976 | Bratzler et al. . |
| 4,011,066 | 3/1977 | Bratzler et al. . |

*Primary Examiner*—Delbert E. Gantz
*Assistant Examiner*—G. E. Schmitkons
*Attorney, Agent, or Firm*—Christie, Parker & Hale

[57] ABSTRACT

Liquified hydrocarbon gases containing at least carbonyl sulfide as an impurity are purified by intimately mixing the liquified hydrocarbon gas with an aqueous absorbent for hydrogen sulfide in a hydrolysis zone maintained at a temperature and a pressure sufficient to maintain the liquified hydrocarbon gas in the liquid state and hydrolyze the carbonyl sulfide to hydrogen sulfide and carbon dioxide. The liquified hydrocarbon gas containing at least a portion of the formed carbonyl sulfide and carbon dioxide is separated from the liquid absorbent and passed to an absorption zone where it is contacted with a liquid hydrogen sulfide absorbent where at least the formed hydrogen sulfide is separated from the liquified petroleum gas. A stage of absorption of at least hydrogen sulfide may proceed mixing of the liquified hydrocarbon gas with the absorbent in the hydrolysis reaction zone. The absorbent employed does not combine irreversibly with carbonyl sulfide, hydrogen sulfide, and carbon dioxide, and preferably is an aqueous solution of diethanolamine.

18 Claims, 1 Drawing Figure

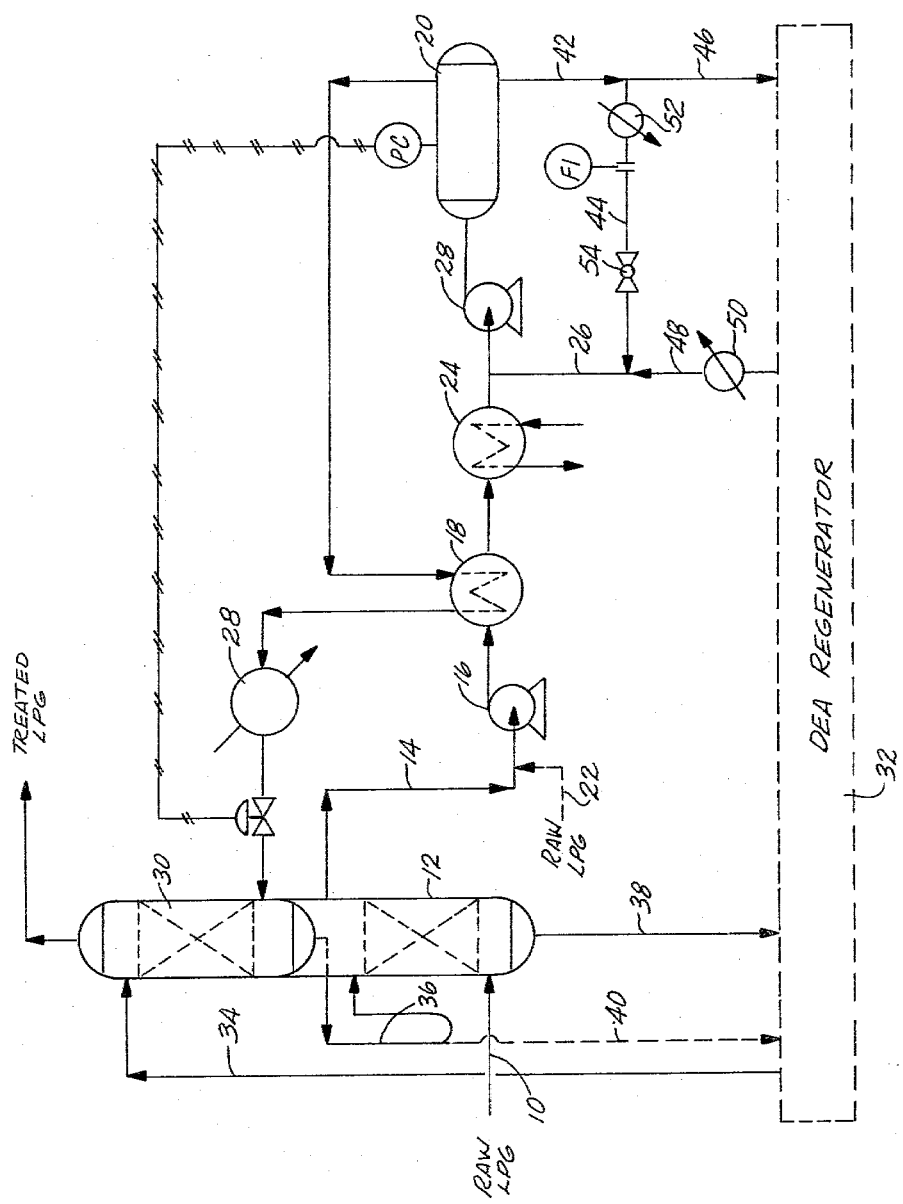

PROCESS FOR REMOVAL OF CARBONYL SULFIDE IN LIQUIFIED HYDROCARBON GASES WITH ABSORPTION OF ACID GASES

BACKGROUND OF THE INVENTION

The removal of carbonyl sulfide from liquified hydrocarbon gases consisting principally of $C_3$ hydrocarbons, $C_4$ hydrocarbons and their mixtures is troublesome and costly. Usually, the stream will also contain hydrogen sulfide, which is readily removable from the gas stream. If, however, the carbonyl sulfide is allowed to remain in the liquified petroleum hydrocarbon and if water is present, it will, with time, undergo the hydrolysis reaction:

$$COS + H_2O \rightarrow H_2S + CO_2$$

to yield hydrogen sulfide which will make the liquified hydrocarbon gas off specification.

While the reaction is reversible, the reaction equilibrium constant is so high that if equilibrium is achieved, the COS becomes insignificant and the $H_2S$ becomes the significant sulfur species.

In U.S. Pat. No. 2,594,311 to Johnson et al, there is described the use of a solution of caustic soda containing a small percentage of monoethanolamine to effect removal of COS at elevated temperatures. The carbonyl sulfide reacts irreversibly with the reagent, causing it to become spent. The products of the reaction must be discarded and replaced, either continuously or in batch quantities. This is costly, both with respect to the cost of replenishing the caustic and the loss of monoethanolamine, which cannot be recovered readily from the spent caustic. In addition to the chemical cost, disposal of the spent materials poses a problem from a pollution standpoint.

It would be desirable, therefore, to provide a process for the purification of liquified hydrocarbon gases, also known in the trade as liquified petroleum gases or LPG, which does not involve high chemical costs or create a problem of pollution to the environment.

SUMMARY OF THE INVENTION

The present invention is directed to a process for purifying liquified hydrocarbon gases containing as an impurity at least carbonyl sulfide and which may also contain hydrogen sulfide and/or carbon dioxide. The process comprises intimately mixing the liquified hydrocarbon gas containing carbonyl sulfide with a liquid aqueous solution of an absorbent for at least hydrogen sulfide which does not combine irreversibly with carbonyl sulfide, hydrogen sulfide, and carbon dioxide in a hydrolysis reaction zone maintained at a temperature sufficient to hydrolyze the contained carbonyl sulfide to hydrogen sulfide and carbon dioxide. This forms a two phase mixture of liquified hydrocarbon gas containing at least a portion of the hydrogen sulfide and carbon dioxide formed by hydrolysis and the liquid aqueous solution of the absorbent containing at least hydrogen sulfide. The liquified hydrocarbon gas containing hydrogen sulfide and carbon dioxide is separated from the liquid aqueous solution of the absorbent containing at least hydrogen sulfide and contacted with a hydrogen sulfide lean aqueous absorbent for at least hydrogen sulfide to separate the hydrogen sulfide from the liquified hydrocarbon gas. The hydrogen sulfide lean aqueous absorbent is at temperatures lower than the temperature of hydrolysis reaction zone.

While a variety of absorbents may be employed, it is preferred to employ as the absorbent an aqueous solution of diethanolamine, preferably a solution containing from about 10 to about 30 percent by weight diethanolamine. Hydrolysis preferably occurs at a temperature from about 120° to about 200° F. while the system is at all times maintained at a pressure sufficient to retain the liquified hydrocarbon gas in the liquid phase.

If the liquified hydrocarbon gas contains appreciable amounts of hydrogen sulfide, the liquified hydrocarbon gas is contacted with an absorbent for hydrogen sulfide, also at a lower temperature than the hydrolysis reaction zone, to remove the bulk of the hydrogen sulfide prior to hydrolysis of carbonyl sulfide.

DRAWINGS

The attached drawing illustrates the process of the present invention in its various embodiments.

DETAILED DESCRIPTION

The present invention is directed to the treatment of liquified petroleum hydrocarbons, also known as liquified petroleum gases or LPG, made up of $C_3$ hydrocarbons, $C_4$ hydrocarbons, and mixtures thereof, to remove the difficult to remove impurity, carbonyl sulfide. The liquified petroleum hydrocarbon (LPG) may also contain sufficient hydrogen sulfide to warrant two absorption stages for its removal. The process will be described in terms of this embodiment. There is employed in the process liquid aqueous solutions of absorbents for at least hydrogen sulfide and, if desired, carbon dioxide, which do not irreversibly combine with hydrogen sulfide, carbon dioxide and carbonyl sulfide. By the term "which do not irreversibly combine with carbonyl sulfide, hydrogen sulfide, and carbon dioxide", as applied to the absorbent, there is meant an absorbent which has at least some solubility for carbonyl sulfide, but which will make the carbonyl sulfide readily available for hydrolysis to release the reaction products, hydrogen sulfide, and carbon dioxide.

While other absorbents may be used, for convenience the invention will be described in terms of the use of aqueous solutions of diethanolamine, the presently preferred absorbent.

With reference now to the Drawing, the liquified hydrocarbon gas (LPG) containing as an acid gas impurity hydrogen sulfide or hydrogen sulfide and carbon dioxide, as well as carbonyl sulfide, is passed in the liquified state under pressure by line 10 to absorption tower 12. There is flowing in absorption tower 12, countercurrent to the flow of liquified petroleum gas, an aqueous solution of diethanolamine (DEA), preferably a solution containing from about 10% to about 30% by weight diethanolamine. The solution in absorption tower 12 is normally maintained at ambient temperature, or less. It may also be operated at higher temperatures, but at a temperature below the temperature at which carbonyl sulfide is hydrolyzed in accordance with this invention. Absorption tower 12 serves to remove the bulk of the hydrogen sulfide and, if present, carbon dioxide from the liquified hydrocarbon gas by contact with the alkaline diethanolamine solution. The pressure in tower 12 and in the entire system is maintained sufficient such that the liquified petroleum gas will not be vaporized upon heating.

After exiting absorption tower 12, the liquified hydrocarbon gas stream is passed by line 14 to pump 16 and through indirect heat exchanger 18 where it serves to receive heat from and to cool a carbonyl sulfide-free stream of liquified hydrocarbon gas exiting settler 20.

Where the raw liquified hydrocarbon gas is essentially free of hydrogen sulfide and carbon dioxide so as not to require their removal from the bulk of the liquid stream, the raw LPG may be fed directly to pump 16 through line 22.

After further heating as required to a temperature sufficiently to hydrolyze the contained carbonyl sulfide in indirect heat exchanger 24, the liquified hydrocarbon gas is combined with a hot solution of diethanolamine, typically at the temperature of hydrolysis of from about 120° F. to about 200° F., introduced by line 26. The combined streams are intimately mixed in centrifugal pump 28 where the contained carbonyl sulfide is hydrolyzed to hydrogen sulfide and carbon dioxide.

The mixture then flows to settler 20 where the liquified hydrocarbon gas and aqueous phases separate. The hot liquified hydrocarbon gas leaves the top of settler 20, passes through heat exchanger 18 to partially heat the feed and, as required, is cooled to a temperature suitable for absorption of acid gases in cooler 28. From there, the liquified petroleum gas containing the products of hydrolysis, namely hydrogen sulfide and carbon dioxide, is brought into liquid-liquid contact with a lean diethanolamine absorbent in countercurrent flow in absorption tower 30 where the contained hydrogen sulfide and carbon dioxide are removed from the liquified hydrocarbon gas.

In this operation, the lean diethanolamine absorbent from diethanolamine regenerator 32 passes by line 34 to tower 30 at a temperature lower than the temperature of hydrolysis. Where two absorption towers are employed, the liquid exits the base of tower 30 and flows by gravity through hydraulic seal 36 to absorption tower 12 from which the spent rich diethanolamine solution is passed by line 38 to diethanolamine regenerator 32. Where only a single tower is employed, the liquid from absorber 36 is passed by line 40 to diethanolamine regenerator 32.

As indicated, the liquified hydrocarbon gas entering tower 30 contains acid gases produced by hydrolysis and any acid gases in the feed and not removed in absorption tower 12, and if absorption tower 12 is not employed, the acid gases contained in the feed. Pressure control (PC) is employed to always maintain the liquified petroleum gas in the liquid state.

Purified liquified petroleum gas flows from the upper section of absorber 30 as a product. The hot diethanolamine solution which separates in settler 20 flows from the bottom of settler 20 by line 42 and may be recycled directly by bypass line 44 or passed, depending upon the condition of the solution, by line 46 to diethanolamine regenerator 32, where it is stripped of the acid gases and returned by line 48. The degree of recycle is controlled by valve 54.

Some of the hydrogen sulfide and carbon dioxide formed in the hydrolysis reaction will be absorbed by the diethanolamine solution circulating through the mixing pump and the settler.

If hydrolysis is sufficiently complete with essentially no replacement of diethanolamine solution required other than to compensate for entrainment in the liquified petroleum gas leaving the settler, this is the only amount which need be replaced from the diethanolamine regeneration facilities, with no other withdrawal required.

If an essentially closed loop consisting of lines 42, 44, and 26 is employed, the diethanolamine solution will be in equilibrium with the absorbed $H_2S$ and $CO_2$, and the $H_2S$ and $CO_2$ generated as a consequence of hydrolysis of the carbonyl sulfide will be substantially retained by the liquified hydrocarbon gas for removal in absorber 30.

If desired, however, diethanolamine regeneration can be employed to aid in removal of the acid gases from the system so as to supplement the operation of absorption tower 30. In this event, all or a portion of the aqueous absorbent leaving settler 20 may be passed by lines 42 and 45 to diethanolamine regenerator for stripping of the acid gases and recycled back by lines 48 and 26 to the system.

If heating is required, it may be supplied by heat exchanger 50. Heat exchanger 52 may also be employed for the closed-loop operation to account for heat losses in the system. Valve 54 is to regulate the flow of the diethanolamine solution during recycle with flow being monitored by flow indicator F1.

The mixing pump 28 provides high dispersion in the intimate contacting of the two liquid phases. Alternately, a mixing valve (not shown) may be employed and, in this instance, a circulating pump for the diethanolamine solution would be inserted in line 26. Hydrolysis is rapid; occurring within about 2 to about 5 seconds at the temperatures employed.

In operation, if no separation of the hot rich diethanolamine solution to regeneration is required because of the employment of a solution in equilibrium with hydrogen sulfide and carbon dioxide such that carbon dioxide and hydrogen sulfide generated from the hydrolysis of carbonyl sulfide are removed from the system with the liquified petroleum gas as rapidly as they are formed, settler 20 may be made small. Recirculation of some of the liquified petroleum gas through the settler circuit will be of no consequence, nor will the carryover of minor amounts of the absorption solution from the top of the settler, since any carryover solution will be taken up in the absorber 30.

For gases rich in carbonyl sulfide, recycling may be desired and in the alternative, the settler 20 can be eliminated. In this operation, there is only one circulation of the diethanolamine solution with settling occurring at the base of absorber 30 to which the mixture of diethanolamine and liquified hydrocarbon gas flow. In this case, the diethanolamine solution may be fed to the system sufficiently hot to eliminate the need for heater 24.

For facilities large enough to make power recovery economically feasible, a recovery turbine may be used for pressure letdown of the liquified hydrocarbon gas leaving the hydrolysis settler 20. The power recovery turbine may be used to drive the pressurizing pump 16 in part or the mixing pump 28 in total.

While the invention has been described in terms of employing aqueous diethanolamine solutions as the absorbent, other absorbents which are substantially non-reactive with respect to carbonyl sulfide may also be employed. They include selective and non-selective absorbents such as methyldiethanolamine; triethanolamine; diisopropanolamine; diglycolamine and the like. Physical absorbents such as glycols; polyethylene glycol, dimethyl ether; Sulfolane; propylene carbonate; N' methyl pyrollidone and the like may also be used alone or in combination with other absorbents.

What is claimed is:

1. A process for purifying liquified hydrocarbon gases containing as an impurity carbonyl sulfide which comprises:
   (a) intimately mixing the liquified hydrocarbon gas containing carbonyl sulfide with a liquid aqueous solution of an absorbent for at least hydrogen sulfide which absorbent does not combine irreversibly with carbonyl sulfide, hydrogen sulfide, and carbon dioxide in a hydrolysis reaction zone maintained at a temperature sufficient to hydrolyze the contained carbonyl sulfide to hydrogen sulfide and carbon dioxide and hydrolyzing the carbonyl sulfide to form a two phase mixture of liquified hydrocarbon gas containing at least a portion of the hydrogen sulfide and carbon dioxide formed by hydrolysis and the liquid aqueous solution of the absorbent containing at least hydrogen sulfide;
   (b) separating the liquified hydrocarbon gas containing hydrogen sulfide and carbon dioxide from the liquid aqueous solution of the absorbent containing at least hydrogen sulfide;
   (c) contacting the liquified hydrocarbon gas containing the hydrogen sulfide and carbon dioxide with a hydrogen sulfide lean aqueous absorbent for at least hydrogen sulfide which does not combine irreversibly with carbonyl sulfide, hydrogen sulfide, and carbon dioxide at a temperature lower than the temperature of the hydrolysis reaction zone to absorb hydrogen sulfide from the liquified hydrocarbon gas.

2. A process as claimed in claim 1 in which the carbonyl sulfide is hydrolyzed at a temperature from about 120° F. to about 200° F.

3. A process as claimed in claim 1 in which the liquid aqueous solution of the absorbent in the hydrolysis reaction zone is in equilibrium with hydrogen sulfide and carbon dioxide and substantially all of the hydrogen sulfide and carbon dioxide formed by hydrolysis of carbonyl sulfide is retained by the liquified hydrocarbon gas.

4. A process as claimed in claim 1 in which at least a portion of the liquid aqueous solution of the absorbent is passed with at least formed hydrogen sulfide from the hydrolysis reaction zone to a regeneration zone where at least part of the contained hydrogen sulfide is removed from the liquid aqueous solution of the absorbent and a hydrogen sulfide depleted liquid aqueous absorbent is recycled for contact with the liquified hydrocarbon gas containing carbonyl sulfide to absorb hydrogen sulfide formed by hydrolysis of carbonyl sulfide.

5. A process for purifying a liquified hydrocarbon gas stream containing as impurities carbonyl sulfide and at least hydrogen sulfide which comprises:
   (a) contacting the liquified hydrocarbon gas stream with a first liquid aqueous absorption solution containing an absorbent for hydrogen sulfide which absorbent does not combine irreversibly with carbonyl sulfide, hydrogen sulfide, and carbon dioxide to absorb, at a first temperature, hydrogen sulfide from the liquified hydrocarbon gas to leave a residual stream of liquified hydrocarbon gas containing carbonyl sulfide;
   (b) intimately mixing the residual stream of liquified hydrocarbon gas containing carbonyl sulfide with a second liquid aqueous solution containing an absorbent for at least hydrogen sulfide which absorbent does not combine irreversibly with carbonyl sulfide, hydrogen sulfide, and carbon dioxide in a hydrolysis reaction zone at a temperature higher than the first temperature and sufficient to hydrolyze the contained carbonyl sulfide to hydrogen sulfide and carbon dioxide and hydrolyzing the carbonyl sulfide to form a two phase mixture of liquified hydrocarbon gas containing at least a portion of the hydrogen sulfide and carbon dioxide formed by hydrolysis of carbonyl sulfide and a second liquid aqueous absorption solution containing hydrogen sulfide; and
   (c) separating the liquidfied hydrocarbon gas containing the hydrogen sulfide and carbon dioxide from the second liquid aqueous absorption solution containing the hydrogen sulfide and contacting, at a temperature lower than the hydrolysis reaction zone, the liquified hydrocarbon gas containing hydrogen sulfide and carbon dioxide with a hydrogen sulfide lean liquid aqueous absorbent for at least hydrogen sulfide which does not combine irreversibly with carbonyl sulfide, hydrogen sulfide, and carbon dioxide, to absorb at least formed hydrogen sulfide from the liquified hydrocarbon gas.

6. A process as claimed in claim 5 in which the carbonyl sulfide is hydrolyzed at a temperature from about 120° F. to about 200° F.

7. A process as claimed in claim 5 in which the second liquid aqueous solution of the absorbent is in equilibrium with hydrogen sulfide and carbon dioxide and substantially all of the hydrogen sulfide and carbon dioxide formed by hydrolysis of carbonyl sulfide is retained by the liquified hydrocarbon gas.

8. A process as claimed in claim 5 in which at least a portion of the second liquid aqueous solution of the absorbent is passed with at least formed hydrogen sulfide to a regeneration zone where at least part of the contained hydrogen sulfide is removed from the second liquid aqueous solution of the absorbent and a hydrogen sulfide depleted second liquid aqueous absorbent is recycled for contact with the liquified hydrocarbon gas containing carbonyl sulfide to absorb hydrogen sulfide formed by hydrolysis of carbonyl sulfide.

9. A process for purifying liquified hydrocarbon gas streams containing as an impurity carbonyl sulfide which comprises:
   (a) intimately mixing the liquified hydrocarbon gas containing carbonyl sulfide with an aqueous solution of diethanolamine in a hydrolysis reaction zone maintained at a temperature sufficient to hydrolyze the carbonyl sulfide to hydrogen sulfide and carbon dioxide and hydrolyzing the carbonyl sulfide to form a two phase mixture of liquified hydrocarbon gas containing at least a portion of the hydrogen sulfide and carbon dioxide formed by hydrolysis of carbonyl sulfide and an aqueous solution of diethanolamine containing hydrogen sulfide and carbon dioxide;
   (b) separating the liquified hydrocarbon gas containing hydrogen sulfide and carbon dioxide from the aqueous solution of diethanolamine containing hydrogen sulfide and carbon dioxide and contacting the liquified hydrocarbon gas containing hydrogen sulfide and carbon dioxide with a lean aqueous solution of diethanolamine to absorb, at a temperature lower than the hydrolysis reaction zone, hydrogen sulfide and carbon dioxide from liquified hydrocarbon gas.

10. A process is claimed in claim 9 in which the hydrolysis is carried out at a temperature from about 120° to about 200° F.

11. A process is claimed in claim 9 in which the aqueous solution of diethanolamine in the hydrolysis reaction zone is in equilibrium with hydrogen sulfide and carbon dioxide and continuously recirculated after separation for mixing with the liquified hydrocarbon gas containing carbonyl sulfide and wherein the liquified hydrocarbon gas contains substantially all of the hydrogen sulfide and carbon dioxide formed by hydrolysis of carbonyl sulfide.

12. A process is claimed in claim 9 in which at least a portion of the second aqueous solution of diethanolamine is passed from the hydrolysis reaction zone to a regeneration zone for elimination of the contained hydrogen sulfide and carbon dioxide and returned for intimate mixing with liquified hydrocarbon gas to absorb hydrogen sulfide and carbon dioxide formed by hydrolysis of carbonyl sulfide.

13. A process claim in claim 9 in which each of the aqueous solutions of diethanolamine contain from about 10 to about 30 percent by weight diethanolamine.

14. A process for purifying a liquified hydrocarbon gas stream containing as impurities carbonyl sulfide and at least hydrogen sulfide which comprises:
 (a) contacting the liquified hydrocarbon gas stream with a first liquid aqueous solution of diethanolamine to absorb, at a first temperature, hydrogen sulfide from the liquified hydrocarbon gas and leave a residual stream of liquified hydrocarbon gas containing carbonyl sulfide;
 (b) intimately mixing the residual stream of liquified hydrocarbon gas containing carbonyl sulfide with a second aqueous solution of diethanolamine in a hydrolysis zone maintained at a temperature higher than the first temperature and sufficient to hydrolyze the carbonyl sulfide to hydrogen sulfide and carbon dioxide and hydrolyzing the carbonyl sulfide to form a two phase mixture of liquified hydrocarbon gas containing at least a portion of the hydrogen sulfide and carbon dioxide formed by hydrolysis of carbonyl sulfide and a second aqueous diethanolamine solution containing hydrogen sulfide and carbon dioxide;
 (c) separating the liquified hydrocarbon gas containing formed hydrogen sulfide and carbon dioxide from the aqueous solution of diethanolamine and contacting, at a temperature lower than the temperature of the hydrolysis reaction zone, the liquified hydrocarbon gas containing hydrogen sulfide and carbon dioxide with the third hydrogen sulfide lean, aqueous solution of diethanolamine to absorb formed hydrogen sulfide and carbon dioxide from liquified hydrocarbon gas.

15. A process as claimed in claim 14 in which the carbonyl sulfide is hydrolyzed at a temperature from about 120° F. to about 200° F.

16. A process as claimed in claim 14 in which the second aqueous solution of diethanolamine is in equilibrium with hydrogen sulfide and carbon dioxide and substantially all of the hydrogen sulfide and carbon dioxide formed by hydrolysis of carbonyl sulfide is retained by the liquified hydrocarbon gas.

17. A process as claimed in claim 14 in which at least a portion of the second aqueous solution of diethanolamine is passed with formed hydrogen sulfide and carbon dioxide to a regeneration zone where at least part of the contained hydrogen sulfide and carbon dioxide are removed from the second aqueous solution of diethanolamine and a hydrogen sulfide and carbon dioxide depleted aqeuous solution of diethanolamine is recycled for contact with the liquified hydrocarbon gas containing carbonyl sulfide to absorb hydrogen sulfide and carbon dioxide formed by hydrolysis of carbonyl sulfide.

18. A process claim in claim 14 in which each of the aqueous solutions of diethanolamine contain from about 10 to about 30 percent by weight diethanolamine.

* * * * *